United States Patent
Lading et al.

(10) Patent No.: US 10,052,036 B2
(45) Date of Patent: Aug. 21, 2018

(54) NON-INTERFERING BLOOD PRESSURE MEASURING

(71) Applicant: QUALCOMM Incorporated, San Diego, CA (US)

(72) Inventors: Lars Lading, Roskilde (DK); David Boettcher Baek, San Diego, CA (US)

(73) Assignee: QUALCOMM Incorporated, San Diego, CA (US)

(*) Notice: Subject to any disclaimer, the term of this patent is extended or adjusted under 35 U.S.C. 154(b) by 554 days.

(21) Appl. No.: 14/714,776

(22) Filed: May 18, 2015

(65) Prior Publication Data

US 2015/0327784 A1  Nov. 19, 2015

Related U.S. Application Data

(60) Provisional application No. 62/000,078, filed on May 19, 2014, provisional application No. 62/072,568,
(Continued)

(51) Int. Cl.
*A61B 5/021* (2006.01)
*A61B 5/00* (2006.01)
(Continued)

(52) U.S. Cl.
CPC ........ *A61B 5/02108* (2013.01); *A61B 5/0059* (2013.01); *A61B 5/0082* (2013.01);
(Continued)

(58) Field of Classification Search
CPC ...... A61B 5/02108; A61B 5/021; A61B 5/022
See application file for complete search history.

(56) References Cited

U.S. PATENT DOCUMENTS

| | | |
|---|---|---|
| 5,309,916 A | 5/1994 | Hatschek |
| 5,406,952 A | 4/1995 | Barnes et al. |

(Continued)

FOREIGN PATENT DOCUMENTS

| | | |
|---|---|---|
| CN | 104138253 A | 11/2014 |
| JP | 2011239972 A | 12/2011 |

(Continued)

OTHER PUBLICATIONS

International Search Report and Written Opinion—PCT/US2015/031538—ISA/EPO—dated Aug. 27, 2015.
(Continued)

*Primary Examiner* — Meredith Weare
(74) *Attorney, Agent, or Firm* — Kilpatrick Townsend & Stockton

(57) ABSTRACT

Systems, methods, and devices of various embodiments enable measurement of blood pressure from an artery. The various embodiments may measure, using a non-interfering arterial measurement sensor, a first change in distension of the artery at a measurement location without interference to an arterial pressure at the measurement location during a series of pulses. A first pulse rate and estimated pulse pressures may be determined from the first change in distension. A coefficient may be determined fitting an exponentially decaying function representing an exponential decay of a portion of a diastolic phase to select ones of the estimated pulse pressures corresponding to the diastolic phase. An absolute blood pressure may be determined by applying the coefficient to a select mathematical model expressing a first relationship between the first change in distension of the artery and the pulse pressure in the artery at the measurement location.

36 Claims, 4 Drawing Sheets

Related U.S. Application Data filed on Oct. 30, 2014, provisional application No. 62/072,601, filed on Oct. 30, 2014.

(51) Int. Cl.
| | |
|---|---|
| *A61B 8/04* | (2006.01) |
| *A61B 5/053* | (2006.01) |
| *A61B 5/11* | (2006.01) |
| *A61B 5/02* | (2006.01) |
| *A61B 5/107* | (2006.01) |

(52) U.S. Cl.
CPC .......... *A61B 5/021* (2013.01); *A61B 5/02116* (2013.01); *A61B 5/0535* (2013.01); *A61B 5/1126* (2013.01); *A61B 5/6898* (2013.01); *A61B 5/725* (2013.01); *A61B 5/726* (2013.01); *A61B 5/7275* (2013.01); *A61B 5/7278* (2013.01); *A61B 5/7282* (2013.01); *A61B 5/7285* (2013.01); *A61B 8/04* (2013.01); *A61B 5/02007* (2013.01); *A61B 5/053* (2013.01); *A61B 5/1075* (2013.01); *A61B 2560/0223* (2013.01); *A61B 2560/0238* (2013.01); *A61B 2560/0242* (2013.01); *A61B 2560/0247* (2013.01); *A61B 2562/0214* (2013.01); *A61B 2562/0219* (2013.01)

(56) References Cited

U.S. PATENT DOCUMENTS

| | | |
|---|---|---|
| 6,322,515 B1 | 11/2001 | Goor et al. |
| 7,674,231 B2 | 3/2010 | McCombie et al. |
| 8,313,439 B2 | 11/2012 | McCombie et al. |
| 8,585,602 B2 | 11/2013 | Crabtree et al. |
| 8,672,854 B2 | 3/2014 | McCombie et al. |
| 8,690,785 B2 | 4/2014 | Lading |
| 2006/0211942 A1 | 9/2006 | Hoctor et al. |
| 2007/0055163 A1 | 3/2007 | Asada et al. |
| 2007/0167844 A1 | 7/2007 | Asada et al. |
| 2007/0197921 A1 | 8/2007 | Cohen et al. |
| 2010/0274143 A1 | 10/2010 | Kim et al. |
| 2011/0009718 A1 | 1/2011 | Gavish |
| 2011/0208066 A1* | 8/2011 | Gnadinger ............ A61B 5/021 600/485 |
| 2015/0327785 A1 | 11/2015 | Lading et al. |
| 2015/0327786 A1 | 11/2015 | Lading |

FOREIGN PATENT DOCUMENTS

| | | |
|---|---|---|
| JP | 2012061131 A | 3/2012 |
| JP | 2013220243 A | 10/2013 |
| WO | 2005065042 A2 | 7/2005 |
| WO | 2014074901 A1 | 5/2014 |
| WO | 2014195578 A1 | 12/2014 |

OTHER PUBLICATIONS

McCombie D B., et al., "Adaptive hydrostatic blood pressure calibration: Development of a wearable, autonomous pulse wave velocity blood pressure monitor", 2007 Annual International Conference of the IEEE Engineering in Medicine and Biology Society : [EMBC '07] ; Lyon, France, Aug. 22-26, 2007 ; [In Conjunction With the Biennial Conference of the Societe Francaise De Genie Biologique Et Medical (SFGB, Aug. 22, 2007 (Aug. 22, 2007), pp. 370-373, XP031336180, ISBN: 978-1-4244-0787-3 abstract.

Bouwmeester J C., et al., "Partitioning pulmonary vascular resistance using the reservoir-wave model", Journal of Applied Physiology, vol. 115, No. 12, Dec. 15, 2013 (Dec. 15, 2013), pp. 1838-1845, XP055207985, ISSN: 8750-7587, DOI: 10.1152/japplphysiol,00750.2013 pp. 1840, 184.

International Search Report and Written Opinion—PCT/US2015/031524—ISA/EPO—Aug. 27, 2015.

Wang J J., et al., "Systemic venous circulation. Waves propagating on a windkessel: relation of arterial and venous wincikessels to systemic vascular resistance", AJP: Heart and Circulatory Physiology, vol. 290, No. 1, Aug. 12, 2005 (Aug. 12, 2005), pp. H154-H162, XP055207961, ISSN: 0363-6135, DOI: 10.1152/ajpheart. 00494.2005 p. H155.

Xuan F.W., "An Exploration on Real-time Cuffless Blood Pressure Estimation for e-Home Healthcare," 2011, 96 pages.

Eiken O., et al., "Blood Pressure Regulation V: In Vivo Mechanical Properties of Precapillary Vessels as Affected by Long-Term Pressure Loading and Unloading," European Journal of Applied Physiology, 2014, vol. 114 (3), pp. 499-509.

* cited by examiner

NON-INTERFERING BLOOD PRESSURE MEASURING

RELATED APPLICATIONS

This application claims the benefit of priority to U.S. Provisional Application No. 62/000,078 entitled "Method of Calibrating a Non-Interfering Continuous Blood Pressure Measurement Device" filed May 19, 2014; U.S. Provisional Application No. 62/072,568 entitled "Continuous Calibration of Non-Interfering Blood Pressure Device" filed Oct. 30, 2014; and U.S. Provisional Application No. 62/072,601 entitled "A Method of Estimating the Transmural Pressure in an Artery of a Subject with a Non-Interfering Continuous Blood Pressure Measuring Device" filed Oct. 30, 2014, the entire contents of each of which are hereby incorporated by reference.

BACKGROUND

Devices for measuring cardiovascular properties suffer from the problem that the measurement itself interferes strongly with the state of the subject, thereby leading to erroneous results. This is especially the case for current cuff-based methods that may impart a significant physiological impact. In current cuff-based methods, the systolic blood pressure is obtained by completely or at least substantially blocking an artery, which in most cases is the brachial artery in the upper arm. Blocking the artery affects pulse pressure propagation and pulse pressure shapes, which may only be tolerated in the peripheral system. Further, the diastolic pressure is derived from measurements obtained when the transmural pressure (pressure difference between the outside and the inside of an artery) is close to zero, which implies those measurements are made under conditions that are far from normal.

Additionally, blood pressure often exhibits considerable variability over time. Thus, identifying diurnal or other temporary variations in blood pressure may be very important for proper diagnosis of hypertension. It has also recently been shown that performing ambulatory blood pressure measurements is overall cost-effective.

It is therefore desirable to provide a device for measuring blood pressure that does not interfere with the normal bodily functions or at least does not perturb an artery being measured and that may measure blood pressure continuously and over long periods.

SUMMARY

Systems, methods, and devices of various embodiments enable measurement of blood pressure from an artery without interfering with arterial pressure at the measurement location. The various embodiments may measure, using a non-interfering arterial measurement sensor, a first change in distension of the artery at a measurement location without interference to an arterial pressure at the measurement location during a series of pulses. A first pulse rate and estimated pulse pressures may be determined from the first change in distension. A coefficient may be determined fitting an exponentially decaying function representing an exponential decay of a portion of a diastolic phase to select ones of the estimated pulse pressures corresponding to the diastolic phase. An absolute blood pressure may be determined by applying the coefficient to a select mathematical model expressing a first relationship between the first change in distension of the artery and the pulse pressure in the artery at the measurement location.

BRIEF DESCRIPTION OF THE DRAWING

The accompanying drawings, which are incorporated herein and constitute part of this specification, illustrate exemplary embodiments of the claims, and together with the general description given above and the detailed description given below, serve to explain the features of the claims.

DETAILED DESCRIPTION

Figure 1:
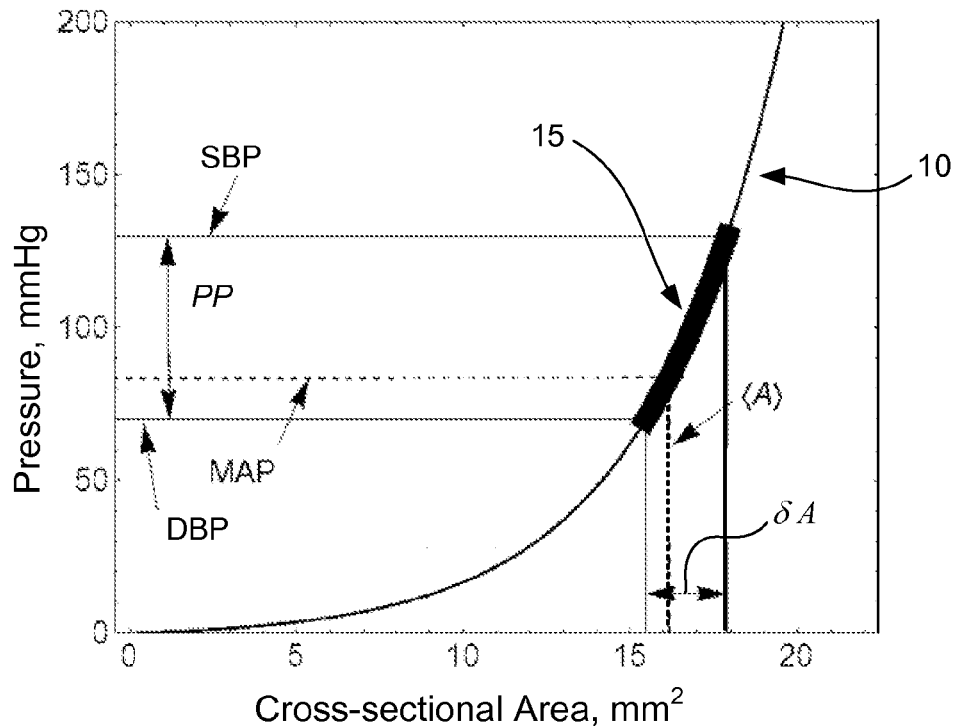
FIG. 1 is a graph of a stress-strain relationship for an artery comparing pressure versus an arterial cross-sectional area according to various embodiments.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

Various embodiments include methods, systems, and devices for measuring blood pressure from an artery in a limb of a subject without requiring a reference device (e.g., an inflatable cuff). Various embodiment methods may include measuring a change in distension of the artery from a location on the limb without interference to a pulse pressure in the artery at the measurement location during a series of pulses. Various embodiment methods may determine a pulse rate and a pulse pressure from the change in distension. Various embodiment methods may also determine a previously unknown coefficient needed to determine accurately blood pressure by curve fitting to an exponential decay of a diastolic phase of the pulse pressure. In addition, other unknown parameters, such as sensor measuring biases, may be determined by taking advantage of physiological characteristics of the venous system. An absolute blood pressure in the artery at a measured location may then be calculated by applying the determined coefficient and measuring bias to a mathematical model that expresses a relationship between changes in distension of the artery and pulse pressure.

Various embodiments include a blood pressure measuring device that provides an output (e.g., a measured quantity) that varies proportionally with variations of distension of an artery at a measurement location. The proportionality may reflect incremental changes or fluctuations and not the absolute values of the quantity measured because of bias inherent in the measuring device and/or the arterial system. To address this, the various embodiments determine the bias as part of the coefficient determined by curve fitting to the exponential decay of the diastolic phase of the measured pulse pressure. The determined coefficient may account for the sensitivity of the measuring device and the physical properties of the arteries, and thus may be used to convert a measured quantity to a more accurate absolute pressure.

Various embodiments determine an absolute blood pressure in an arterial system based on an understanding of the bio-mechanisms in the human body using the mathematical relationships disclosed herein to calculate the blood pressure indirectly. While the same general mathematical relationship may be used for many patients, the specific parameters of the relationship may be unique for each patient. Thus, various embodiments determine the parameters of the relationship through a calibration procedure. Without a proper calibration, the conversion between a measured parameter of an artery and blood pressure is not reliable.

Various embodiments provide a method of adjusting (e.g., for calibration) a non-interfering blood pressure measuring devices that takes into account the changes to the arterial elastic properties over time. Various embodiment methods may include an initial calibration, a continuous calibration, or a combination of both. Various embodiment methods may start with a non-calibrated model, and adapt the model over time to arrive at a calibrated model, which may also adapt to changes in the arterial properties of the subject.

As used herein, the term "pulse pressure" refers to the pressure in the arterial system close to the heart of a subject. This value is generally not affected by local changes in the hydrostatic pressure in the peripheral regions of the body of the subject.

As used herein, the term "transmural pressure" refers to the pressure difference between the pressure inside an artery and directly outside the artery at a specific location in a specific artery. The transmural pressure will be dependent on the hydrostatic pressure due to the height of the specific location. For example if a measuring device is attached to the wrist of a subject, then moving the wrist up and down will cause significant changes in the transmural pressure measured at the measuring location whereas the pulse pressure will be relatively unaffected by the slow up and down motion of the wrist. In addition, without an externally applied counter pressure (e.g., inward pressure from an inflatable cuff) the transmural pressure may be presumed to be approximately equal to the blood pressure.

The term "absolute arterial pressure" is used herein to define the actual pressure in an artery at a specific location and at a particular time. In most cases the absolute arterial pressure will be very close to the transmural pressure at the same location, if no significant external pressure is applied to the artery (i.e., only atmospheric pressure is applied).

The term "blood pressure" is used herein as a general term to refer to a pressure in the arterial system of the subject. For the sake of this specification, the transmural pressure, the pulse pressure, and the absolute arterial pressure are all considered "blood pressures." For example, devices that measure the transmural pressure at a specific location and devices that measure the pulse pressure may be used to measure blood pressure.

As used herein, the expression "constant pulse rate" refers to a pulse rate that over a period of several heartbeats does not change significantly. In this respect, a beat-to-beat variation may be as high as 50% and still be considered a constant pulse rate. Thus, an average of the pulse rate over a certain amount of time may be used. For example, a pulse rate measured over 30-60 seconds may be considered constant if variations over that period are below 10%. Alternatively, an upper limit of variation may be used, such as 5%, 2%, or 1%. As a further alternative, a moving average over a certain amount of time may be used, for example over 1 minute. As yet a further alternative, a limit on the maximum amount of change in a moving average of the pulse rate in a certain amount of time may be used. This may be related to the derivative/slope of the moving average of the pulse rate.

As used herein, the expression "non-interfering" refers to a device that does not interfere with the normal bodily functions or at least does not perturb an artery being measured. A continuous measuring device may be used over a long period (e.g. over 1-24 hours), such that blood pressure readings may be taken over a longer period. When the pressure is monitored over a longer period, then one can see changes in the pressure over time, which may provide significant information about the subject. Some non-limiting examples of sensors are ultrasound sensors, bioimpedance sensors, and photoplethysmographic sensors.

As used herein, the term "measuring device" refers to a physical apparatus attached to a subject for taking measurements of a biometric. In contrast, the term "sensor" generally refers to a device that responds to a physical stimulus (as heat, light, sound, pressure, magnetism, or a particular motion) and transmits a resulting impulse (as for measurement or operating a control). A sensor may measure changes in position, size, and/or composition, such as within an organ or a portion of a body. In addition, the term "arterial measurement sensor" more specifically refers to a component of the measuring device, which directly performs the actual measurement of a physical characteristic of an artery of the subject, such as fluctuations in blood flow and/or the cross-sectional area of an artery. For example, the measuring device may include one or more arterial measurement sensors and an electronic processing device for processing signals from the arterial measurement sensor and/or communicating with external equipment.

The terms "computing device" are used herein to refer to any one or all of cellular telephones, smart-phones, webpads, tablet computers, Internet enabled cellular telephones, Wi-Fi enabled electronic devices, laptop computers, dedicated healthcare electronic devices, personal computers, and similar electronic devices equipped with at least a processor and configured to communicate with a blood pressure measuring device described herein, such as a negligible interfering and negligible perception configuration or form blood pressure measuring device (e.g., a wearable patch, bracelet, anklet, watch, etc.).

The word "exemplary" is used herein to mean "serving as an example, instance, or illustration." Any implementation described herein as "exemplary" is not necessarily to be construed as preferred or advantageous over other implementations.

As used herein, the term "repeatedly" with reference to measurements taken may refer to a plurality of measurements done periodically, with a fixed period between measurements. Alternatively, one or more non-periodic intervals may be used between measurements.

Stress-strain properties of arterial walls may be highly non-linear. At low pressures, an arterial vessel is very elastic, dominated by elastin fibers. At higher pressures, an arterial vessel appears stiffer, dominated by collagen fibers. A very coarse classification of arteries is muscular or elastic, although most arteries may be a combination thereof. The larger arteries in the central system are predominantly elastic, whereas the arteries in the peripheral system are predominantly muscular. The peripheral arteries are generally thinner and stiffer than the arteries in the central system and the elastic properties are more dependent on the smooth muscles than in the central arteries. These smooth muscles are arranged in a spiral pattern, presumably arranged in such a way that the arterial expansion upon a pressure increase is predominantly in the radial direction and negligible in the longitudinal direction. Artery walls are in general much stiffer than the surrounding tissues. In this way, the pressure right outside the artery is essentially the same as the pressure outside the limb, if no external pressure is applied.

In addition, the elastic properties of an artery may vary over time, particularly since the tension of the muscles in the artery typically changes over time according to the state of the person. Further, a number of substances may affect the tension of the muscles in an artery. For example, nitroglycerin relaxes smooth muscles, which generally decreases stiffness therein and may cause arteries to expand in diameter even when a pressure in the artery remains constant or decreases.

Some contemporary blood pressure measuring devices measure the distension of an artery, which is a measure of the expansion or change in diameter of the artery synchronous with the heartbeat. Accurately converting the measure of distension into an absolute blood pressure requires knowledge of certain properties of the artery. In particular, it is usually required to know at least the stiffness or elasticity of the artery in order to convert dimensional characteristics like distension into a measure of blood pressure. However, estimating and/or determining such arterial properties using conventional techniques is not straightforward. In addition, conventional techniques generally interfere with (i.e., perturb) the artery being measured.

Previous attempts at providing non-interfering continuous blood pressure measuring devices have suffered from calibration problems since arterial properties change so frequently. With the wrong calibration, a determination of pressure from dimensional characteristics like the cross-sectional area of an artery may be inaccurate. Some solutions that acknowledge the variation in arterial properties over time suggest recalibration at regular intervals. However, such recalibration is inconvenient to the subject, requiring that the subject actively take part in the recalibration while remaining at rest and relaxed.

A technical problem addressed by various embodiments is how to adjust the parameters used to determine blood pressure from non-interfering measurements of arterial dimensions while taking into account variations in arterial properties over time, as well as accounting for measuring biases from devices used to measure the arterial dimensions.

FIG. 1 is a graph of a stress-strain relationship for an artery, which includes an exponential curve 10 (e.g., in accordance with equation (1)) representing a stress-strain relationship of an artery. The exponential curve 10 is a plot of the cross-sectional area of an artery (in mm²) on the horizontal axis versus the transmural pressure (in mmHg) on the vertical axis. Equation (1) is a mathematical model expressing a relationship between a cross-sectional area of an artery and a typical pressure range present in an artery of a subject, such as a living human being or an animal. Alternatively, other functions may be used to approximate the stress-strain relationship of an artery. A normal operating portion 15 (denoted by a thicker portion of the exponential curve 10) is defined at an upper end by a systolic pressure SBP and at a lower end by a diastolic pressure DBP. A difference between the systolic and diastolic pressures (i.e., the maximum and minimum pressures in a pulse respectively) reflects a pulse pressure δP. Further, the right end of the normal operating portion 15 represents a maximum cross-sectional area of the artery corresponding to the systolic pressure SBP, while the left end of the normal operating portion 15 of the curve represents a minimum cross-sectional area of the artery corresponding to the diastolic pressure DBP. A difference between the maximum and minimum pressures reflects a distension δA of the artery. A vertical dotted line in FIG. 1 represents a mean arterial cross-sectional area <A>, whereas a horizontal dotted line reflects the mean arterial pressure (MAP).

Modeling the Stress-Strain Relationship

An exponential mathematical model may generally express the stress-strain relationship in large regions like the peripheral arteries. Other stress-strain relationships may alternatively be used (e.g., bilinear), but the relationship between pressure and arterial lumen may generally be modeled as a monotonic relation; that is to say that an increase in pressure is necessarily accompanied by an increase in cross-sectional area of an artery.

In this way, positive transmural pressures may generally be represented by the following exponential relation:

$$P=P_o(e^{A/A_o}-1) \qquad (1),$$

where $P_o$ and $A_o$ are parameters that are dependent on the measured artery, P is the transmural pressure, and A is the cross-sectional area of the artery at a particular measuring location. The parameters $P_o$ and $A_o$ reflect specific properties (e.g., elasticity) of the measured artery at a particular point in time, since many properties of arteries change over time. Equation (1) may be limited to circumstances in which the cross-sectional area A is greater than the arterial parameter $A_0$ ($A \geq A_0$). In addition, equation (1) may not be valid for very large transmural pressures (e.g., >200 mmHg) or very low (e.g., <20 mmHg or negative transmural pressures. However, for the region of pressures encountered in living human beings, equation (1) may be a good representation of the stress-strain relationship.

Considering that the properties of arterial walls generally change over time, the stress strain relationship of those arterial walls may also experience temporal changes. Since various embodiment measuring devices may use a stress strain relationship to relate a measured cross-sectional area to blood pressure (e.g., equation (1)), the parameters in the stress strain relationship may be adjusted to reflect such changes over time, at least incrementally. Without adjusting the stress-strain relationship, calculations of pressure may not be reliable.

When trying to convert measurements from peripheral arteries into values of blood pressure, many unknown variables need to be determined. The parameters $P_o$ and $A_o$ in equation (1) may take into account those unknown variables but are not themselves always known or easily determined. Various embodiments manipulate the stress-strain relationship used to determine blood pressure from arterial dimensions, taking advantage of certain anatomical phenomena, to reduce the number of unknown parameters and provide a way to measure blood pressure without interfering with the absolute arterial pressure. In this way, various embodiments take advantage of assumptions regarding how the arterial stress-strain relationship changes over time.

Various embodiments adapt the mathematical model used to express the stress-strain relationship of the artery by taking advantage of certain situations in which a change in a physical characteristic of an artery may be observed without a corresponding change in blood pressure. These situations may result from a change in the properties of the arteries that occur when blood pressure is constant. However, without being able to measure directly the blood pressure (i.e., using a non-interfering blood pressure measuring device), another indicator may be used that reflects on the pressure and indicates when the blood pressure is constant.

Considering that equation (1) is used to express the stress-strain relationship in the peripheral arteries, a slope of equation (1) may express the change in the stress-strain relationship over time. The slope for equation (1) may be expressed by a derivative of the transmural pressure dP divided by the derivative of the cross-sectional area dA, which may be expressed as:

$$\frac{dP}{dA} = \frac{P_o}{A_o} \exp^{A/A_o}. \qquad (2)$$

While equation (1) may not be appropriate for values of the cross-sectional area A below zero, values at or slightly above zero may represent a slope at very low pressures. An initial slope of equation (2) may thus include a cross-sectional area A of the artery that is slightly above or almost zero (A≈0). In this way, the initial slope of equation (2) may reflect a ratio of the parameters $P_o$ and $A_o$ (e.g., $P_0/A_0$). The initial slope of equation (2) may take into account the elastic properties of the elastin in the arteries. At low expansions of the artery, the smooth muscles are not yet activated and the elastic properties of the artery are generally controlled by the elastin. While properties of the elastin may change over long periods (i.e., years), over short periods it may be presumed to be constant. This assumption may be particularly applicable to the time spans involved in measuring/monitoring blood pressures (i.e., less than 24 hours). In contrast, the smooth muscles may change their properties in less than a minute. It thus may be advantageous to rewrite the mathematical models used to express arterial properties in such a way that one parameter is associated with elastin and one with smooth muscles.

Various embodiments assume that a ratio of the unknown parameters $P_0/A_0$ is constant, which allows the ratio of the unknown parameters to be replaced with a constant C. Equation (1) may then be rewritten to include the constant C as follows:

$$P = CA_0(e^{A/A_0} - 1) \qquad (3).$$

In equation (1), both of the parameters $P_0$ and $A_0$ need to be determined if both parameters change over time. However, by recognizing circumstances in which the ratio of the parameters is constant, equation (3) shows that the transmural pressure P may be expressed as a function of only the cross-sectional area A, and the arterial parameter $A_0$. In this way, adjustments to the determination of a transmural pressure P may only demand the adjustment of one parameter in the mathematical model over time, instead of two.

An inverse of equation (3) expresses the cross-sectional area A as a function of pressure, as follows:

$$A = A_0 \ln\left(\frac{P}{A_0 C} + 1\right). \qquad (4)$$

A gradient of equation (4) may be expressed as:

$$\frac{dA}{dP} = \frac{A_0}{A_0 C + P}. \qquad (5)$$

During an average pulse pressure, an approximation to the gradient may be expressed by the distension divided by the pulse pressure as follows:

$$\frac{\delta A}{\delta P} \cong \frac{A_0}{A_0 C + \langle P \rangle}, \qquad (6)$$

where $\langle P \rangle$ is the average of the mean arterial pressures over several pulses. The "mean arterial pressure" as used herein refers to the average arterial pressure in a single pulse.

Previous Value Conditions

In principle, all the elements in equation (6) except for the constant C are functions of time. However, in situations in which the average pulse rate does not change, both the mean arterial pressure <P> and the pulse pressure δP may be assumed to similarly not change. Hence in various embodiments, instead of using a current pressure value, the pressure value from a previous determination may be used. However, since the arterial parameter $A_0$ may have changed from a previous value, the distension δA may have also changed. Thus, solving equation (6) for an instance of the arterial parameter $A_0$ yields:

$$A_{0,i} = \frac{\langle P_i \rangle \delta A}{\delta P_i - C \delta A_i} = \frac{\langle P_{i-1} \rangle \delta A}{\delta P_{i-1} - C \delta A_i}, \qquad (7)$$

where a current value subscript i denotes a term that corresponds to current values and a previous value subscript i−1 denotes a term that corresponds to values from a previous observation. From equation (1), the pulse pressure may be expressed as:

$$\delta P = e^{A/A_0} C \delta A \qquad (8).$$

In addition, since the exponential part for any value of A is larger than unity, and typically much larger, the distension δA multiplied by the constant C (i.e., C δ A) may be assumed to be substantially smaller than the pulse pressure δP for arteries where the elastic properties are dominated by the smooth muscles. Thus, neglecting such substantially smaller terms in the denominator confirms equation (7) may be an accurate approximation in situations in which the stress-strain relationship may not be expressed well by equation (1).

Estimation of the variations in the stress-strain relationship, characterized by the instantaneous arterial parameter $A_{0,1}$, may be improved upon by applying a predictive filter or observer such as a Kalman filter as used in guidance systems and control systems.

Carry Forward Conditions

Various embodiments assume that if a first transmural pressure is known under a particular set of conditions, although conditions may change, the subsequent transmural pressure may be equal to the first transmural pressure when that particular set of conditions is again observed. Thus, once the subject's resting heart rate is known, the transmural pressure should again be the same specific value each time the same resting heart rate is observed. As soon as the heart rate changes, the value of the transmural pressure may no longer be assumed to be the same. However, once the subject's heart rate returns to the subject's resting heart rate, the transmural pressure may again be presumed equal to the previously calculated transmural pressure. In this way, determinations of pressure or other parameters may carry forward.

Carrying forward values of pressure or other parameters may be useful for calibration procedures. For example, at time 0 a calibration procedure may be performed that measures a heart rate of 70 beats per minute. Based on the calibration procedure, a calibration pressure $P_C$ and a calibration pulse pressure $\delta P_C$ may be determined. Subsequently, even though the subject's heart rate may have gone up to 90 beats per minute for some time, once a constant pulse rate of 70 beats per minute is again observed the calibration pressure $P_C$ and the calibration pulse pressure $\delta P_C$ may be used. In this way, the calibration values may be carried forward and used similar to the "previous values" in equation (7). Thus, the previous value terms (i.e., with subscript i−1) in equation (7) may be replaced with calibration values as follows:

$$A_{0,i} = \frac{\langle P_i \rangle \delta A_i}{\delta P_i - C \delta A_i} = \frac{\langle P_c \rangle \delta A_i}{\delta P_c - C \delta A_i}. \tag{9}$$

Using previous or carry forward values may be helpful when a constant calibration heart rate is measured. However, when a constant heart rate that is different from the calibration heart rate is measured, the mathematical model used to express the stress-strain relationship of the arteries may need adjusting.

Hydrostatic Pressure Adjustment

The effect of a change in hydrostatic pressure, from a known change in height of a measurement location, may be readily determined. When the elevation of the measurement location changes by a known distance, a current value of hydrostatic pressure will have changed from a previous value at the measurement location. Thus various embodiments assume that if the pulse rate is constant, the blood pressure will also remain constant, which implies that any change in blood pressure at the measuring site as a result of a height change may be primarily associated with the hydrostatic pressure change. Thus, an adjustment for the change in hydrostatic pressure may be incorporated into an expression of the average of the mean arterial pressures as follows:

$$\langle P_i \rangle = \langle P_{i-1} \rangle + \Delta P_H = \langle P_{i-1} \rangle = \rho g \Delta h \tag{10},$$

where $\Delta P_H$ is the hydrostatic pressure change, $\rho$ is a density of the fluid (i.e., the blood density), g is the gravitational acceleration (i.e., 9.8 m/s$^2$), and $\Delta h$ is a distance corresponding to the change in elevation (i.e., a height change).

If an expected hydrostatic pressure change due to the height change $\Delta h$ is identical to the measured pressure change, then no change to the parameters defining the stress-strain relationship need be made. However, a variation between the expected pressure change and the measured pressure change may be used to determine an incremental adjust a parameter of the stress-strain relationship, such as the arterial parameter $A_0$ defining the gradient in equation (5). Thus, a change in hydrostatic pressure may be used to adjust the parameters of the mathematical model used to express the stress-strain relationship of the arteries. Such a hydrostatic pressure adjustment of the mathematical model may be performed after a discontinuity in the pulse rate is observed, but only after the pulse rate is again constant.

Alternatively, a hydrostatic pressure adjustment may be performed by comparing an expected change in cross-sectional area of an artery at a measurement location due to the hydrostatic pressure change to the actual change measured in the cross-sectional area. Using the stress-strain relationship of equation (4), an expected pressure may be used to solve for an expected cross-sectional area. Thus, if the expected cross-sectional area derived from the stress-strain relationship is different from a measured cross-sectional, the arterial parameter $A_0$ may be adjusted accordingly.

The actual adjustment of the arterial parameter $A_0$ may be performed in accordance with various known techniques. For example, control theory based techniques may be used when the error between the expected signal and the measured signal is used to change the arterial parameter $A_0$.

Incremental Sensitivity Adjustment

Various embodiments recognize that an output X of a measuring device may include a measurement bias. For example, a blood pressure measuring device may be calibrated to measure a quantity monotonically related to a physiological parameter, such as the cross-sectional area A, of an artery arranged in the vicinity of an arterial measurement sensor of the blood pressure measuring device. The measured cross-sectional area A may generally be modelled as a function of the output X (i.e., A=f(X)), but may include a number of unknown parameters, like the measurement bias. In addition, using a stress-strain relationship expressing the pressure P as a function of the cross-sectional area A (e.g., equation (1)), the pressure P may also be estimated directly as a function of the output X (i.e., P=f(X)). However, the measurement bias remains an unknown parameter. In order to determine changes in this unknown parameter, various embodiments may exploit conditions, such as a constant heart rate. As noted above with regard to the hydrostatic pressure adjustment, various embodiments exploit the known effects of hydrostatic pressure in order to determine an adjustment that may account for changes (i.e., an incremental sensitivity) in the measurement bias.

The output X of a measuring device may include an output change $\Delta X$, which may be observed jointly with a change in conditions, such as a height change $\Delta h$ of the measurement location. While the measurement bias may change with movements of the measurement location, measurement bias changes may not occur immediately. Rather, various embodiments assume measurement bias changes may occur relatively slowly (e.g., on time scales of at least several minutes, which may result from relatively slow variations in the properties of the veins of a subject). Thus, when the output change $\Delta X$ and elevation change $\Delta h$ occur during a period in which the pulse rate is constant (disregarding very short-term heart rate variability), deviations from expected changes may be attributable to an incremental sensitivity k. In this way, the incremental sensitivity k reflects an incremental variation at a given point on a stress-strain curve and relates an incremental change in pressure to an incremental output change. Thus, a linear relationship between the incremental values of the hydrostatic pressure change $\Delta P_H$ versus the output change $\Delta X$ may be expressed as:

$$\Delta P_H = k(\Delta X) \quad (11).$$

Thus, various embodiments may determine the incremental sensitivity k by exploiting the effects of hydrostatic pressure changes. Determining the incremental sensitivity k enables the conversion of distension measurements to an estimated pulse pressure even though conditions have changed, such as from initial calibration conditions.

Fitting to the Exponential Decay of the Diastole

Imposing hydrostatic pressure changes during a period of constant heart rate may be useful for determining the incremental sensitivity k (assumed to be constant) and may be used to convert an output X to an estimated pulse pressure. However, only knowing the incremental sensitivity k does not provide a direct determination of the absolute arterial pressure or the mean arterial pressure. Thus, in order to obtain a correction for a possible additive measurement bias, the exponential decay of the arterial pressure during the diastole phase may be exploited.

Figure 2:
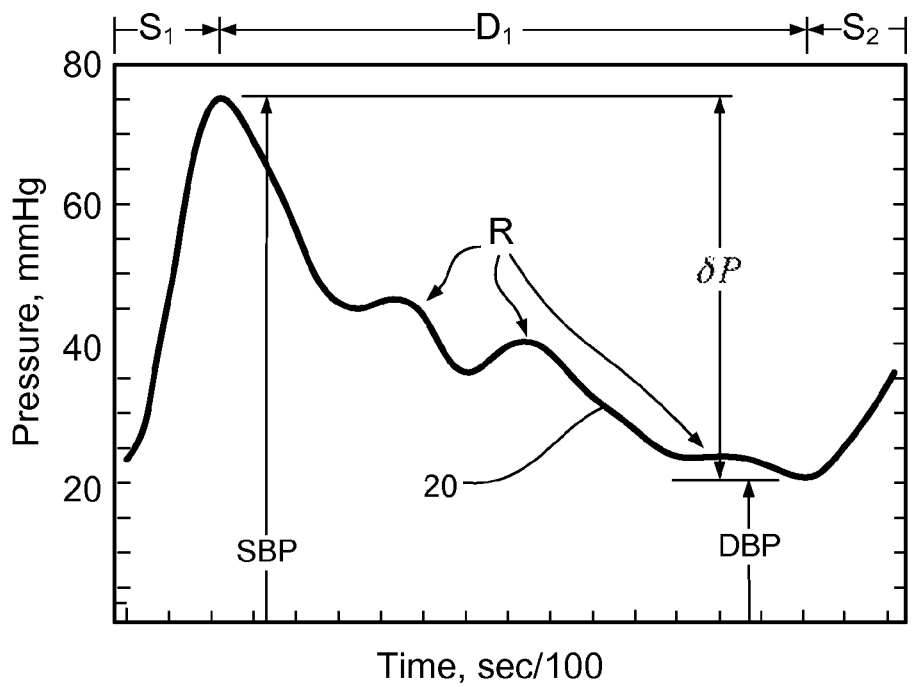
FIG. 2 is a graph of pressure versus time for a pulse pressure of an initial pulse and the start of a subsequent pulse, noting particular elements according to various embodiments.

FIG. 2 is a graph of a pulse pressure 20 showing the changes in pressure (i.e., the vertical axis, measured in mmHg) over time (i.e., the horizontal axis, measured in sec/100). Pressure pulses occur after each contraction of the left heart ventricle and are considered as having three parts. A first part $S_1$, referred to as the systolic phase, reflects the immediate rise of the pressure as a consequence of the ejection from the heart.

The second part $D_1$, referred to as the diastolic phase, reflects the fall of the pressure after the systolic phase. The diastolic phase is generally characterized by an exponentially decaying pressure. The exponential decay asymptotically approaches the venous pressure, but is redirected before doing so upon the occurrence of the subsequent pulse, which starts the next pulse's systolic phase $S_2$. The exponential decay may be caused by the arterial system being connected with the veins through capillary network with a high fluid-flow resistivity and the veins being much more elastic than the arteries. Thus, the venous system essentially behaves like a capacitor, which has a capacitance much larger than that of the arterial system. Propagation effects may play an insignificant role for the decay since a time-constant of the decay may be much larger than the pulse propagation time through the arterial system.

The pulse pressure 20 also includes reflections R, considered the third part, that result from discontinuities in the arterial system, such as bifurcations or diameter changes.

Figure 3:
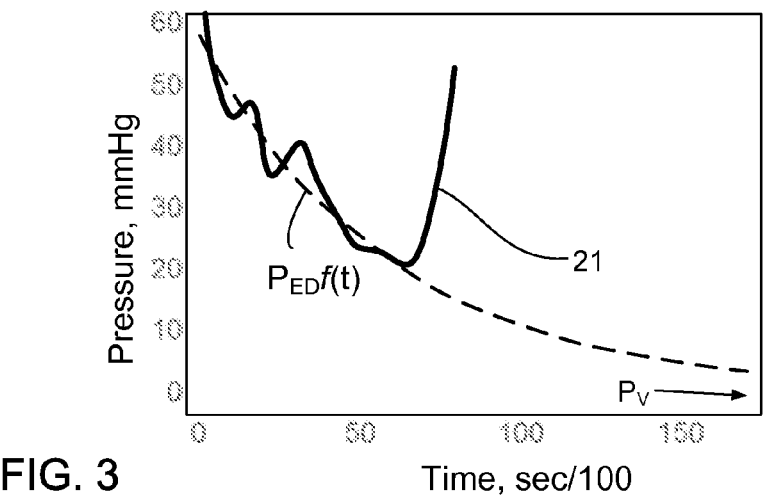
FIG. 3 is a graph of pressure versus time for a pulse pressure of a diastolic phase of an initial pulse and the start of a subsequent pulse, along with a curve matching an exponential decay of the diastolic phase according to various embodiments.

FIG. 3 is a graph of another pulse pressure 21 showing the changes in pressure (i.e., the vertical axis, measured in mmHg) over time (i.e., the horizontal axis, measured in sec/100) during a diastolic phase and part of a subsequent systolic phase. Superimposed on the pulse pressure 21 is a decaying exponential function $P_{ED}f(t)$, expressing the exponential decay of the pulse pressure 21 during and extended well beyond the diastolic phase. An extrapolation of exponentially decaying pressures $P_{ED}$ (i.e., the pressures during the diastolic portion of the pulse pressure) over time may be express as:

$$P_{ED} = a\exp\left(-\frac{t}{t_0}\right) + b, \quad (12)$$

where a represents a distension amplitude of the diastolic phase, t represents a length of time, and $t_0$ represents a time-constant of the decay. The time-constant of the decay $t_0$ may reflect the resistance of the capillary network connecting an artery to veins in conjunction with the capacity of the veins. Equation (12) also includes an asymptotic value b that represents the underlying vein pressure contributions.

Various embodiments determine estimated values of exponentially decaying pressures $P_{ED}$, using the incremental sensitivity k applied to measured values corresponding to the diastolic phase of a pulse. In this regard, consideration need not be given to estimated pulse pressures not corresponding to the diastolic phase (e.g., the systolic phase). A plot of the estimated exponentially decaying pressures $P_{ED}$ may be used to determine a coefficient that fits the exponential decay function of equation (12) to the estimated exponentially decaying pressures $P_{ED}$. Assuming the distension amplitude a may be determined along with the incremental sensitivity k, and considering that the venous pressure may be very low, the determined coefficient may be an additive (or subtractive) value that substantially represents the asymptotic value b in equation (12). The determined coefficient may be very different from the venous pressure, due to biases inherent in most measuring schemes, many of which may be relatively large. Nonetheless, a value of the underlying venous pressure may be used in determining the coefficient by subtracting that value from the asymptotic value b determined from the curve fitting. Thus, the determined asymptotic value b minus the venous pressure may equal the coefficient applied to the otherwise estimated values of pulse pressure to determine an absolute arterial pressure.

In this way, various embodiments fit the exponentially decaying function $P_{ED}f(t)$ to the pulse pressure estimates corresponding to diastolic phases. The fitting procedure may be a least-squares procedure, or may be based on fitting a straight line to the logarithm of the data values with the expected asymptotic value added, and other well known curve-fitting methods may be used. The diastole may be defined as starting at the time instance after the first dip of the pulse in which the second derivative of the measured pulse waveform with respect to time is positive and ending at the onset of the subsequent pulse.

Diastolic, Systolic, and Mean Arterial Pressures

In various embodiments, the distension amplitude a and the asymptotic limit b of equation (12) may be converted to pressure parameters by multiplication with the incremental sensitivity k, which relates incremental measurement variations to pressure variations. In various embodiments, the diastolic blood pressure (DBP) may be estimated by evaluation of equation (12) at the end of the diastole (see FIGS. 2 and 3), multiplying with the incremental sensitivity k, and adding the vein pressure, which may be assumed to be 4 mmHg with an uncertainty of 2 mmHg. The diastolic blood pressure estimate may be performed on the individual pulses and averaging the values of a number of pulses. The number of pulses may be from one to 60 or more. Generally, 60 pulses may be used because short term fluctuations may be minimized and arterial properties may be generally constant over a period of 60 pulses. The diastolic blood pressure estimate may also be obtained from the pulse obtained by conditional averaging. In a similar manner, an estimated pulse pressure $\delta P$ may be obtained directly from Eq. (1) with averaging as described above.

Various embodiments apply a relationship between the systolic pressure (SBP), the diastolic blood pressure (DBP) and the pulse pressure $\delta P$ as follows:

$$SBP = DBP + \delta P \quad (13).$$

Various embodiments determine the Mean Arterial Pressure (MAP) by finding the mean of the pulses from the start of the systole to the end of the diastole, scaled with the incremental sensitivity k and the coefficient determined by fitting to the exponential decay of the diastole. Alternatively, an approximation may be used according to:

$$MAP = \frac{2}{3}DBP + \frac{1}{3}SBP. \quad (14)$$

In various embodiments, parameters characterizing the relation of pressure to measured signal as defined by equation (11) may be determined based on the mean measured signal as recorded at several elevations. The mean measured signal may be a representation of the average signal over a time that may be at least equal to the length of one pulse. A longer time, such as the average signal over a time equal to at least one respiration period, may eliminate the modulation of the blood pressure that is generally caused by respiration. An upper limit for the averaging time may be the time within which the pulse pressure stays constant or is disturbed by movement artifacts. This time may be inferred from the variability of the pulse rate.

In various embodiments, sets of data representing the hydrostatic pressure relative to the heart level and the arterial measurement sensor averaged output may be recorded for several different elevations, providing a data set $\{P_{Hi}, X_i\}$, where the index i indicates the specific elevation. The data set $\{P_{Hi}, X_i\}$ may be used to determine the incremental sensitivity k expressed by equation (11), noting that the absolute arterial pressure P may equal the hydrostatic pressure $P_H$ plus the MAP at an elevation identical to the elevation of the heart. In this way, the pulse pressure $\delta P$ may be determined by measuring the output change $\Delta X$ of the measured quantity X, which may be converted to the absolute arterial pressure using equation (11).

Continuous measurement instructions to the subject may only be feasible at the initialization of a measuring session, as measuring sessions may last 24 hours or longer. Updating the calibration may be needed in the course of a measuring session, which may be achieved by measuring the distension signal, the pulse rate, and the elevation of the measuring location continuously. In response to determining that the elevation changes with a constant pulse rate and the accordingly calculated change of pressure deviates from a threshold value, such as a pressure value associated with the actual measured distension, an update calibration condition may be determined and the device may enter a calibration mode.

Non-Interfering Blood Pressure Measuring Device

Various embodiments include a non-interfering blood pressure measuring device. As mentioned above, physical characteristics of an artery, such as the cross-sectional area A, may be measured with an arterial measurement sensor. Such measurements may be used to measure changes in arterial properties. Thus, changes in an arterial cross-sectional area over a pulse, which represent distension of the artery, may be quantified by the difference between the maximum and minimum cross-sectional areas over the pulse.

Figure 4:
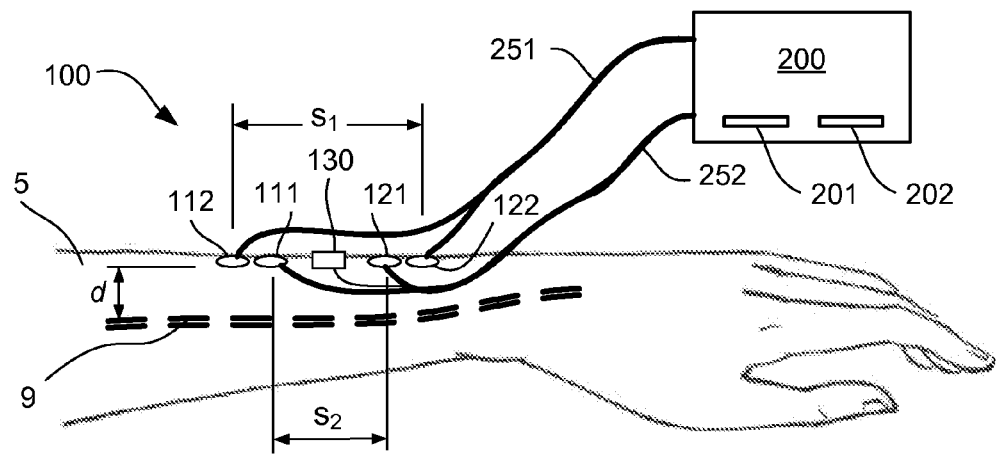
FIG. 4 is a schematic diagram of a device for determining blood pressure placed on a limb of a subject according to various embodiments.

FIG. 4 illustrates a device 100 configured to measure blood pressure from an artery 9 in a limb of a subject 5 in accordance with various embodiments. The device 100 may be placed at a particular location on the subject 5 being measured (i.e., a select portion of the subject's body). For example, the device 100 may include sets of individual patches (each including one or more sensors), separated from one another. Alternatively, the device 100 may include a more unitary structure that wraps partially or completely around a limb of the subject 5. The measuring device may be formed as an elastic band that incorporates a patch with electrodes and a 'pocket' for an electronic unit. Such an elastic band may be sized to ensure relatively low levels of counter pressure (i.e., inwardly from a surface of the skin) to ensure the underlying artery is not perturbed.

The device 100 may include sensors, such as sets of electrodes 111, 112, 121, 122 and one or more elevation sensors 130. The sets of electrodes 111, 112, 121, 122 may be used for measuring one or more parameters using bioelectric impedance, and a control unit 200 coupled to the electrodes for processing data. A first set of electrodes may include a first inner detection electrode 111 and a first outer excitation electrode 112. Similarly, a second set of electrodes includes a second inner detection electrode 121 and a second outer excitation electrode 122. The electrodes 111, 112, 121, 122 may be positioned on a portion of skin of the limb of the subject 5. The second set of two outer excitation electrodes 112, 122 may be placed with an outer separation distance $S_1$ between the electrodes somewhat larger than the depth d at which the artery 9 is embedded in the limb. At the wrist, the depth d may be less than 1 cm, but the separation may be considerably larger, only confined by the length of the limb. The first set of two inner detection electrodes 111, 121 may be placed with an inner separation distance $S_2$, which is less than the outer separation distance $S_1$ and disposed between the two outer excitation electrodes 112, 122. The inner separation distance $S_2$ may be approximately equal to the depth d of the artery or greater. At the wrist, the inner separation distance $S_2$ may be from 5 mm to several centimeters. For example, the inner separation distance $S_2$ may be approximately 2.5 cm and the outer separation distance $S_1$ may be approximately 5 cm. Measurements may be performed on the radial artery or ulna artery within the wrist.

In the various embodiments, an elevation sensor 130 may provide an output that may be continuously converted to a measure of the elevation of the measuring location. For example, the elevation sensor 130 may be a 3D inertial sensor, such as an accelerometer, in which elevation changes may be inferred from integration of the accelerometer output. Other examples of elevation sensors may include barometers magnetic near-field devices, or any other type of sensor configured to measure the elevation or a change in elevation of a measurement location.

An instantaneous elevation or change in elevation may be obtained by double integrating an acceleration signal, such as provided by an accelerometer on the device or placed at the measuring location. The estimation of elevation or change in elevation may be further validated by a level signal provided by an angular sensor mounted on the device or at the measurement location since a horizontal level implies a higher likelihood for a position of the measuring site around the middle of the dynamic range for the elevation. A vertical position implies a high likelihood for being at one of the extremes of the elevation.

In the various embodiments, variations of the hydrostatic pressure (for example an elevation difference of 60 cm will correspond to a 47 mmHg pressure change, while the Mean Arterial Pressure at heart level may be around 100 mmHg) may be continuously monitored along with outputs from the elevation sensor 130, such as a 3D accelerometer with measurements integrated in order to detect position changes, a high resolution barometer configured to output the elevation of the measuring location, etc. When the subject's pulse rate is constant, a "driving pulse pressure" may be assumed to be unchanged and the pulse pressure may be assumed to be constant, and thus the only pressure change may be caused by the change of the hydrostatic pressure due to changes in elevation of the measuring location. This presumption that the only cause of the change in pressure is the change of the hydrostatic pressure may enable determining blood pressure, as well as calibration of a blood pressure measuring device, for incremental changes.

In various embodiments, the device 100 may include a control unit 200, which may register and/or process outputs from the electrodes 111, 112, 121, 122 and/or the elevation sensor 130. Values from sensor measurements may be stored in a memory 202. The control unit 200 may regulate and/or control the timing and/or output levels of the electrodes 111, 112, 121, 122. The control unit 200 may include one or more processors 201 configured to make intermediate and/or final calculations and determinations regarding blood pressure measurements. While the control unit 200 is illustrated as a single unit, multiple control units may be provided. Although connections 251, 252 are illustrated as wired connections, the control unit 200 may include one or more wireless connections, such as using one or more wireless transceivers and antennas.

Figure 5:
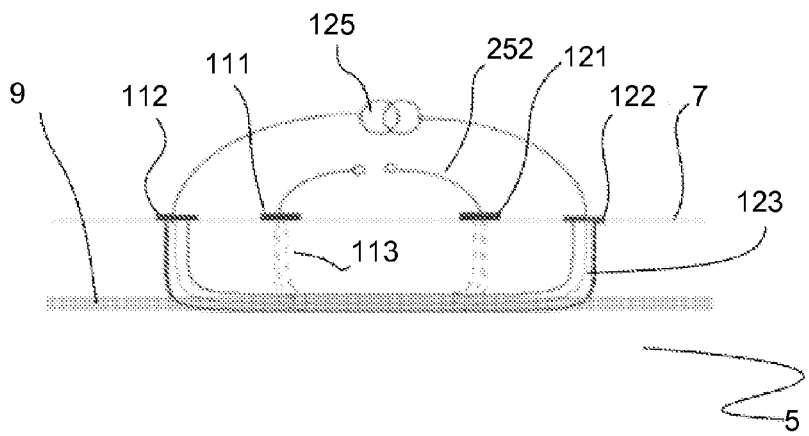
FIG. 5 is a schematic diagram of an arrangement of electrodes on a limb operating to detect distension according to various embodiments.

FIG. 5 is a schematic diagram of the workings of electrode arrangements of the device 100 illustrated in FIG. 4. In some embodiments, a current generator 125 may generate a current that oscillates at a particular frequency. The current generator 125 may be located near the subject (not shown) or inside a control unit (e.g., 200 in FIG. 4). A current from the current generator 125 may be directed into the limb of the subject 5 through the second set of two outer excitation electrodes 112, 122, providing an excitation signal 123. The current from the current generator 125 may be at a frequency in the range of 10 kHz to 10 MHz, or higher. The magnitude of the current may be, for example, in the range of 0.1 mA to 2 mA. In various embodiments, the two outer excitation electrodes 112, 122 may be sized to ensure placement over the underlying artery without knowing the precise location of the underlying artery, which may be displaced laterally to one side or another. An oscillating current from the current generator 125 may generate the excitation signal 123 (i.e., excitation field lines), that start essentially perpendicular to the skin surface 7. As the excitation signal 123 extends away from the skin surface 7, because the skin and the subcutaneous fat have low conductivities and blood has higher conductivity, the excitation signal 123 becomes more aligned with the longitudinal direction of the artery 9. Thus, close to and inside the artery 9 the excitation field lines of the excitation signal 123 are aligned with the direction of the blood inside the artery 9.

The first set of two inner detection electrodes 111,121 may generate a detection signal 113 configured to detect the excitation signal 123 and characteristics thereof. Since the excitation signal 123 is aligned in the central region with the longitudinal direction of the artery 9. The detection signal 113 may be used to measure changes in the excitation signal 123, which allows measurement of changes to physical characteristics of the artery, like cross-sectional area A and distension.

The electrodes 111, 112, 121, 122 may be any shape, including rectangular, oval, or annular, and may be sized appropriately to the body part on which they will be applied. For example, the electrodes 111, 112, 121, 122 may have an overall diameter of approximately 1 mm to 20 mm. In this way, the size of the electrodes 111, 112, 121, 122 may be smaller than the separation distances $S_1, S_2$. The virtual field lines generated by the excitation signal 123 and detection signal 113 may overlap. In this way, the overlap may define an effective detection region, from where impedance variations may be measured by the detection electrodes 111, 121. Signals from the detection electrodes 111, 121 may be recorded and analyzed by a processor (e.g., 201), such as one contained in the control unit (e.g., 200). The outputs of the signals from the two inner electrodes 112, 111 may reflect the distension of the artery between the two electrode locations.

A demodulation of the signals to/from the electrodes 111, 112, 121, 122 may be performed by quadrature detection. In quadrature detection, the detected signals may be mixed with quadrature components of a reference signal derived from the same oscillator that provides the excitation signal to the limb of the subject 5. In general an in-phase part of the demodulated signal may typically be the dominant part reflecting the fact that the real part of the detected impedance is dominating. However, the quadrature component may also be detected and a weighted quadratic sum of the in-phase and quadrature components, respectively, can be applied in order to enhance detection efficiency in cases in which the imaginary part of the impedance is considered important. The imaginary part may be associated with the real parts of the dielectric constants of the relevant tissues, which normally include skin, fat, muscles, and blood.

The signals may be filtered in order to minimize the effect of noise but also to enhance those parts of the signal that are most important for timing: i.e. those parts with a large temporal gradient. The filters for the electrodes 111, 112, 121, 122 may have identical phase characteristics in order to avoid any bias in the estimation of the transit time. Digital finite impulse response filters may be used since the phase characteristics may be accurately controlled due their sampling frequency (e.g., 100-500 Hz).

Figure 6:
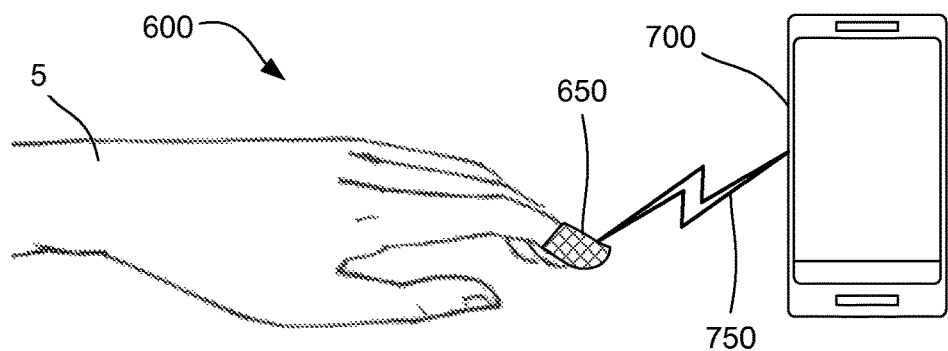
FIG. 6 is an illustration of a device for determining blood pressure placed on a fingertip of a subject, working with a computing device, according to various embodiments.

FIG. 6 illustrates a device 600 configured to determine blood pressure in an artery of a subject 5 in accordance with various embodiments. The device 600 may include a sensor sleeve 650 applied to a fingertip. The sensor sleeve 650, which may encircle a finger may apply a minor constant counter pressure, but still not perturb the underlying arterial pressure. The constant counter pressure may be considered "minor" as long as it is below a diastolic pressure (~90 mmHg) of the subject. The counter pressure may be below 60 mmHg and may preferably be closer to 25 mmHg, which is far more comfortable to the subject. Such a minor constant counter pressure, which may be comparable to the pressure applied by compression stockings, will generally be substantially lower than the pressure applied by an inflatable cuff-type blood pressure device (~200 mmHg). In addition, the application of the minor constant counter pressure may stabilize the veins without hampering a return blood flow. Further, as a result of the minor constant counter pressure, a measurement signal may become larger because of slight modifications to the stress-strain relationship.

The sensor sleeve 650 may include electrodes similar to device 100 (see, FIG. 4) or other sensors for measuring the parameter(s) in contact with the user's skin. In this way, electrodes (i.e., sensors) may be integrated into the inside surface of the sensor sleeve (i.e., configured to face the subject's skin when worn thereon), which presses against the skin. In this way, a firm and even engagement between the skin and the sensor may be maintained.

A computing device 700, remote from the sensor sleeve 650, may operate as a control unit and be wirelessly coupled to the sensor sleeve 650 for processing data. The computing device 700 may be a smartphone, watch-phone, or tablet, laptop or other computer. The sensor sleeve 650 may include its own processor and transceiver for communicating with the computing device 700. In this way, data processing may be performed onboard the sensor sleeve 650, in the computing device 700 operating as a control unit, or a combination of both. In addition, the sensor sleeve 650 may have a separate power source, such as by wire coupling to a nearby source of power (e.g., electrical outlet or battery).

In various embodiments, the location of the measuring device, the location of the sensor (referred to herein as the "measurement location"), and the location of the measured artery may be within close proximity of one another. However, the measurement location does not necessarily have to be coincident with the location of the measurement device. For example, various embodiments may include an ultrasound-based sensor, which performs the measurement on a particular location at a distance from the sensor itself.

Various types of devices may be used to measure dimensional characteristics of an artery. Some examples include devices that employ a technology such as ultrasound, nuclear magnetic resonance, propagating electro-magnetic waves, optical sensing, and/or bioelectrical impedance. Ultrasound may be used to measure distension of an artery wall or flow velocity (i.e., a Doppler velocimetry). Nuclear magnetic resonance may also be used to measuring distension. Other techniques include various devices capable of detecting a propagation property of electro-magnetic waves. In addition, optical instruments may be used to detect and measure distension (e.g. photoplethysmography) or flow velocity. As described above with reference to FIGS. 4 and 5, bioelectrical impedance may be measured, particularly in applications in which distension may be detected from the bioelectrical impedance variations. Additional devices suitable for measuring dimensional characteristics of an artery may be used in accordance with various embodiments.

Figure 7:
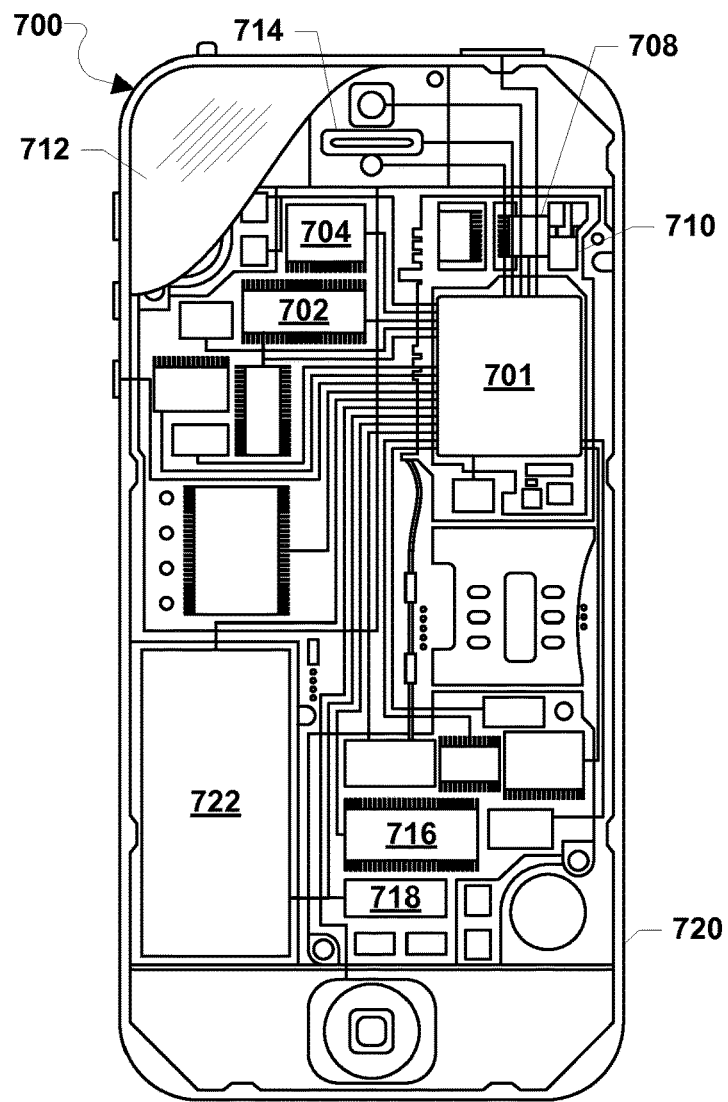
FIG. 7 is a component block diagram of a control unit in the form of a computing device according to various embodiments.

An embodiment blood pressure measuring device may be configured to transmit data to any of a variety of computing devices. For example, FIG. 7 illustrates a computing device 700 suitable for use in various embodiments. The computing device 700 may exchange data to and/or from the blood pressure measuring devices discussed above, such as sensor sleeve 650, and may perform one or more of the operations of method 800 described below. For example, DBP, δP, SBP, MAP, and/or measured pulses, hydrostatic pressure, and/or elevation may be sent from the blood pressure measuring device to the computing device 700.

In various embodiments, the computing device 700 may include a processor 701 coupled to a touch screen controller 704 and an internal memory 702. The processor 701 may be one or more multicore ICs designated for general or specific processing tasks. The internal memory 702 may be volatile or non-volatile memory, and may also be secure and/or encrypted memory, or unsecure and/or unencrypted memory, or any combination thereof. The touch screen controller 704 and the processor 701 may also be coupled to a touch screen panel 712, such as a resistive-sensing touch screen, capacitive-sensing touch screen, infrared sensing touch screen, etc. The computing device 700 may have one or more radio signal transceivers 708 (e.g., Peanut®, Bluetooth®, Zigbee®, Wi-Fi, RF, cellular, near field, etc.) and antennae 710, for sending and receiving, coupled to each other and/or to the processor 701. The transceivers 708 and antennae 710 may be used with the above-mentioned circuitry to implement the various wireless transmission protocol stacks and interfaces. The computing device 700 may include a cellular network wireless modem chip 716 that enables communication via a cellular network, such as an eMBMS network, and is coupled to the processor. The computing device 700 may include a peripheral device connection interface 718 coupled to the processor 701. The peripheral device connection interface 718 may be singularly configured to accept one type of connection, or multiply configured to accept various types of physical and communication connections, common or proprietary, such as USB, FireWire, Thunderbolt, or PCIe. The peripheral device connection interface 718 may also be coupled to a similarly configured peripheral device connection port (not shown). The computing device 700 may also include speakers 714 for providing audio outputs. The computing device 700 may also include a housing 720, constructed of a plastic, metal, or a combination of materials, for containing all or some of the components discussed herein. The computing device 700 may include a power source 722 coupled to the processor 701, such as a disposable or rechargeable battery. The rechargeable battery may also be coupled to the peripheral device connection port to receive a charging current from a source external to the computing device 700.

Processors of computing devices suitable for use in various embodiments may be any programmable microprocessor, microcomputer or multiple processor chip or chips that can be configured by processor executable instructions (applications/software) to perform a variety of functions, including the functions of the various embodiments described above. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store the application software instructions. In many devices, the internal memory may be a volatile or nonvolatile memory, such as flash memory, or a mixture of both. For the purposes of this description, a general reference to memory refers to memory accessible by the processors including internal memory or removable memory plugged into the various devices and memory within the processors.

Figure 8:
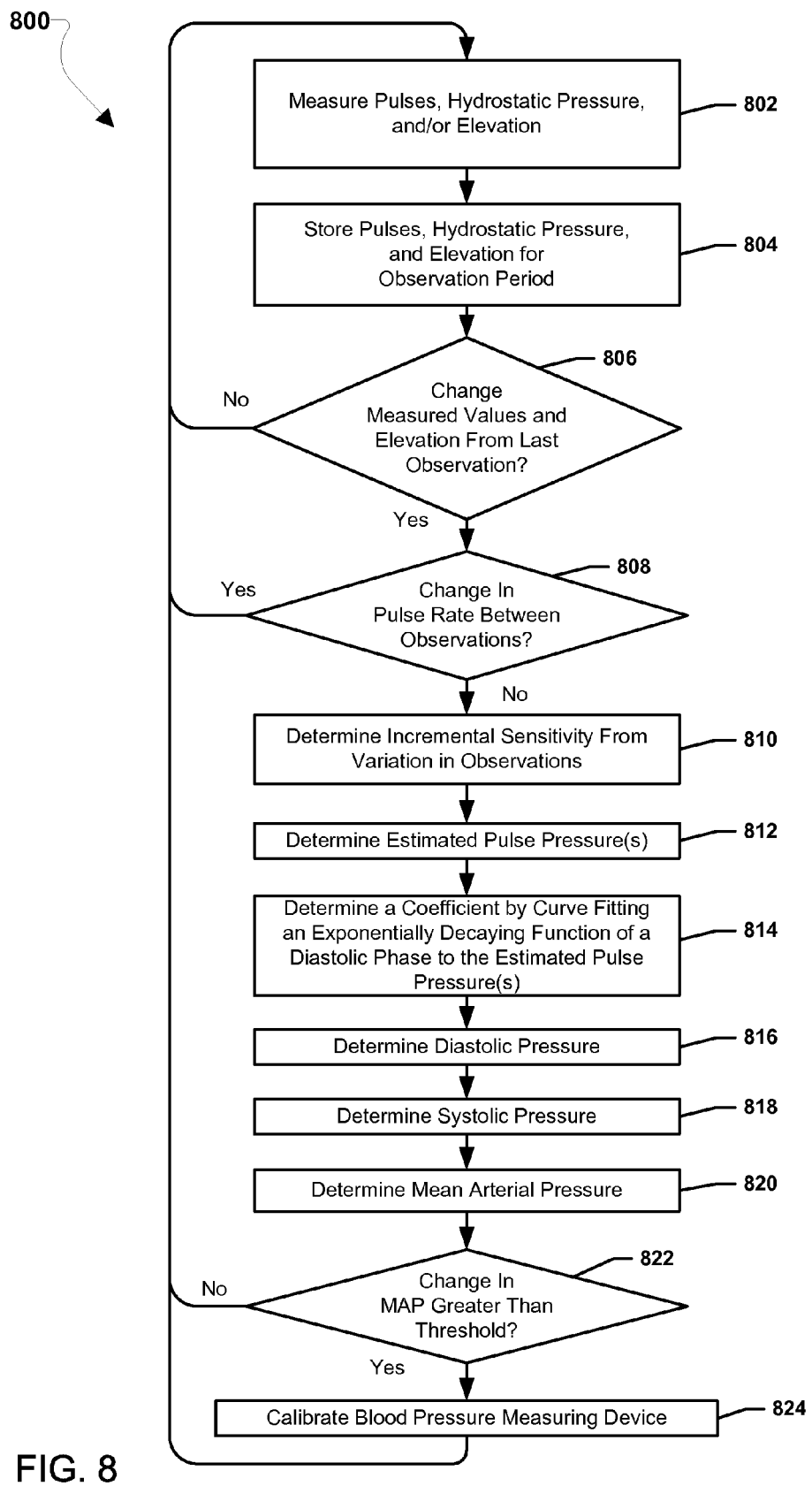
FIG. 8 a process flow diagram illustrating an embodiment method for measuring blood pressure according to various embodiments.

FIG. 8 illustrates a method 800 for blood pressure from an artery in limb of a subject according to various embodiments. With reference to FIGS. 1-8, various operations of the method 800 may be performed by a blood pressure measuring device (e.g., 100, 600), including one or more sensor(s) (e.g., 111, 112, 121, 122, 130, 650), and a control unit (e.g., 200, 700) or other computing device and/or processor in communication with a blood pressure measuring device, such as blood pressure measuring device 100, 600 described above.

In block 802, a sensor may measure pulses, estimate hydrostatic pressure, and elevation at a location of measurement on a limb (e.g., an arm, leg, wrist, ankle, finger, toe, etc.) of a subject, as described above. The sensor may include more than one sensor, such as one sensor for measuring pulses and another sensor for measuring elevation. In various embodiments, a processor may measure pulses, estimate hydrostatic pressure, and elevation based on outputs from one or more sensors, such as an arterial measurement sensor and/or elevation sensor. In various embodiments, the pulses, hydrostatic pressures, and elevation may be obtained as part of an initial calibration, as needed, periodically, and/or continuously. In various embodiments, the processor may average measured elevations over a predetermined period (e.g., a few seconds) and the pulses and hydrostatic pressure may be averaged over that same period.

In block 804, the processor may store the measured pulses, hydrostatic pressures, arterial distension, and elevation and averaged measurements thereof corresponding to an observation period. In an embodiment, the pulses may recorded be continuously as they occur, and the pulse rate may be measured and averaged over a sliding window, such as a thirty-second window to about a two-minute window. For example, the processor may store the measured pulses, hydrostatic pressures, and elevation, as well as averaged measurements thereof, in a memory corresponding to one or more different observation times.

In determination block 806, the processor may determine whether a change in measured values of the artery (e.g., measured values associated with a change in distension and/or a cross sectional area of the artery) and elevation both occurred since the last observation. In various embodiments, the processor may compare the measured values or an average measurements thereof for the most recent observation time to measured values or an average measurements thereof for a previous observation time to determine whether any change has occurred in the measured values, and may compare the elevation from the most recent observation time to the elevation from the previous observation time to determine whether any change has occurred in the elevation. For example, when a change in elevation of the measurement location occurs, the distension of an artery measured at the different elevations may be different, and the change in elevation and measured values may both be determined by comparing the most recent observation and previous observation. In response to determining that no change has occurred in either the distension or the elevation (i.e., determination block 806="No"), the processor may continue to measure pulses, hydrostatic pressure, arterial distension, and elevation in block 802.

In response to determining that a change has occurred in both the distension and the elevation (i.e., determination block 806="Yes"), the processor may determine whether a change in pulse rate has occurred between observation times in determination block 808. A change in elevation and distension without a change in pulse rate may indicate that the only reason for a change in blood pressure is the change in hydrostatic pressure, which may provide an estimate of the current relationship between incremental pressure change and incremental change of measured quantities. In response to determining that a change has occurred in pulse rate (i.e., determination block 808="Yes"), the processor may continue to measure pulses, hydrostatic pressure, arterial distension, and elevation in block 802.

In response to determining that no change has occurred in pulse rate (i.e., determination block 808="No"), the processor may determine an incremental sensitivity (i.e., an adjustment term) from variation in observations in block 810. In an embodiment, the incremental sensitivity may be determining using a relationship between the incremental values of the hydrostatic pressure change $\Delta P_H$ versus the output change $\Delta X$ (e.g., equation (11)) from one observation time to another observation time, in which $\Delta X$ is the change of the mean output of the distension sensor between the two observation times.

In various embodiments, two different observation times may be associated with two different elevations of the measurement location. The processor may determine an incremental sensitivity between observations by performing two calculations and comparing the results. The first calculation may determine the expected pressure change caused by a change in the elevation of the measurement location based on the previous calibration and arterial dimension changes, and the second calculation may determine the change in hydrostatic pressure. The processor may compare the expected pressure change caused by the measurement location elevation change based on the previous calibration and arterial dimension measurements to the change in hydrostatic pressure changes. In response to determining that the pressure changes are different, the processor may determine that a new calibration is needed, and the new calibration may be performed from the hydrostatic pressure and the change in the measured quantity averaged over at least one pulse.

In block 812, the processor may determine the pulse pressure δP. In various embodiments, the pulse pressure δP may be estimated by evaluation of the relationship expressed by equation (11) using an average of values of a number of pulses. The number of pulses used in calculating the average may be from one to 60 or more. In general, 60 pulses may be used since short term fluctuations may be minimized and arterial properties may be generally constant.

In block 814, the processor may determine a coefficient for adjusting a stress-strain relationship of the measured artery by curve fitting an exponentially decaying function to estimated pulse pressures, corresponding to the diastolic phase of a pulse, in order to determining a coefficient for the exponential decay function characterizing the observed decay in pressure. In various embodiments, the estimated pulse pressures corresponding to the diastolic phase of measured pulses recorded between the two observation times may be use to fit an exponentially decaying function with an additive coefficient (which may be at least partially related to a measurement bias). In various embodiments, the estimated pulse pressures corresponding to the diastolic phases may be used to fit the exponentially decaying function on each individual pulse and the coefficient(s) determined may then be averaged over a series of pulses, such as 60 pulses. Alternatively, the fitting may be performed on pulses obtained by conditional averaging over a series of pulses, such as up to 60 pulses. The diastole may be defined as starting at the time instance where the second derivative of the measured pulse waveform with respect to time is positive and ending at the onset of the subsequent pulse.

In block 816, the processor may determine the diastolic blood pressure (DBP). In an embodiment, the distension amplitude a and the asymptotic limit b of equation (12) may be converted to pressure parameters by multiplication with the incremental sensitivity k and correcting for the measurement bias. In an embodiment, the diastolic blood pressure may be estimated by evaluation of the relationship expressed by equation (12) at the end of the diastole, multiplying with the incremental sensitivity k, and adding the vein pressure, which may be assumed to be 4 mmHg with an uncertainty of 2 mmHg. The diastolic blood pressure estimate may be performed on the individual pulses and averaging the values of a number of pulses. The number of pulses may be from one to 60 or more. In general, 60 pulses may be used since short term fluctuations may be minimized and arterial properties may be generally constant. The diastolic blood pressure estimate may also be obtained from the pulse obtained by conditional averaging.

In block 818, the processor may determine systolic blood pressure (SBP). In an embodiment, the systolic blood pressure may be estimated by evaluation of the relationship expressed by equation (13) described above.

In block 820, the processor may determine the Mean Arterial Pressure (MAP). In an embodiment, the MAP may be determined by finding the mean of the pulses from the start of the systole to the end of the diastole, scaled with incremental sensitivity k and corrected with the coefficient determined by fitting the exponentially decaying function characterizing the observed decay in the diastolic pressure to pulse measurement values. In various embodiments, the approximation expressed by equation (14) may be used to determine the MAP.

In determination block 822, the processor may determine whether a change in MAP between observations is greater than a threshold. The threshold value may be a predetermined value stored in a memory and may be associated with a varying condition of the subject. For example, the threshold may be a pressure value associated with an actual measured distension. The processor may determine whether the change in MAP is greater than a threshold by subtracting the MAP determined in block 820 from a previously determined MAP and comparing the determined change in MAP to a threshold value associated with the distension of the artery measured in block 802. In response to determining that the change in MAP is at or below the threshold (i.e., determination block 822="No"), the processor may continue to measure pulses, hydrostatic pressure, distension of the artery, and elevation in block 802.

In response to determining that the change in MAP is greater than the threshold (i.e., determination block 822="Yes"), the processor may initiate a calibration procedure in order to recalibrate the blood pressure measuring device. For example, the processor may signal or control the blood pressure measuring device to enter a calibration mode. Upon calibrating the blood pressure measuring device, the processor may continue to measure pulses, hydrostatic pressure, distension of the artery, and elevation in block 802.

The above description has mainly addressed different embodiment methods of measuring blood pressure from an artery in a limb of a subject with a non-interfering continuous blood pressure measuring device. Various embodiment methods may start by providing a reference model and performing an initial calibration. In response to completing an initial calibration, various embodiment methods may look for periods in which the heart rate is constant. During these periods, the calibration may be adjusted to adapt the parameters of the model to take into account the time varying properties of the arterial system of the subject.

In some embodiments, the device may be attached to the subject without any initial calibration being performed. When device is attached to a subject the system may begin measuring the cross-sectional area of the artery. During periods of constant heart rate, the device may perform calibration procedures based on the hydrostatic pressure if simultaneous height changes of the measuring location are registered.

In various embodiments, if not enough data points are collected to enable an accurate fitting of the model, one or more of the various method operations described above may be performed or repeated.

In various embodiments, the non-interfering measuring device may be attached to a subject without any initial calibration. After a certain amount of time has passed, the device may be completely calibrated and start recording measured values of pressure in a database. Prior to being completely calibrated, the device need not record any values of pressure in the database, or maybe record values of pressure in a database, but mark them with an insecurity factor.

In various embodiments, the non-interfering measuring device may be programmed with an initial calibration or with an initial set of parameters, which are statistically close to a large number of subjects. This initial "rough" calibration may then be adapted via adaptation algorithms over time. In another embodiment, the initial "rough" calibration may be determined by matching a number of physical parameters of the subject to a database of test subjects and choosing the parameters of the test subject that are closest to the subject.

The foregoing method descriptions and the process flow diagrams are provided merely as illustrative examples and are not intended to require or imply that the operations of various embodiments must be performed in the order presented. As will be appreciated by one skilled in the art, the order of operations in the foregoing embodiments may be performed in more than one order. Words such as "thereafter," "then," "next," etc. are not intended to limit the order of the operations; these words are simply used to guide the reader through the description of the methods. Further, any reference to claim elements in the singular, for example, using the articles "a," "an," or "the" is not to be construed as limiting the element to the singular.

While the terms "first" and "second" are used herein, for example to describe electrodes or other elements, such identifiers are merely for convenience and are not meant to limit various embodiments to a particular order, sequence, type of network or carrier.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the various embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

The functions in the various embodiments may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present invention is not intended to be limited to the embodiments shown herein but is to be accorded the widest scope consistent with the following claims and the principles and novel features disclosed herein.

What is claimed is:

1. A method of measuring blood pressure from an artery in a limb of a subject, comprising:
   measuring, by a non-interfering arterial measurement sensor, a first change in distension of the artery at a measurement location on the limb without interference to an arterial pressure at the measurement location during a series of pulses;
   determining, by a processor, a first pulse rate and estimated pulse pressures in response to measuring the first change in distension, the estimated pulse pressures comprising pressure values during at least a portion of a pulse including a diastolic phase;
   determining, by the processor, a coefficient fitting an exponentially decaying function representing an exponential decay of a portion of the diastolic phase to select ones of the estimated pulse pressures corresponding to the diastolic phase, the coefficient indicative of a non-zero asymptotic value of the exponentially decaying function; and
   determining, by the processor, an absolute blood pressure by applying the coefficient to a select mathematical model expressing a first relationship between the first change in distension of the artery and a transmural pressure in the artery at the measurement location.

2. The method of claim 1, further comprising:
   measuring, by an elevation sensor, a change in elevation of the measurement location in response to moving the limb;
   determining, by the processor, an incremental sensitivity between a second change in distension of the artery from the measurement location on the limb and a predicted change in the estimated pulse pressures after the change in elevation; and
   determining, by the processor, the estimated pulse pressures using another mathematical model describing a second relationship between changes in distension and transmural pressure with the incremental sensitivity applied to the another mathematical model.

3. The method of claim 2, wherein the predicted change in distension is based on a last measured physiological parameter at a first elevation and a hydrostatic pressure change corresponding to the change in elevation.

4. The method of claim 1, further comprising:
   determining a second pulse rate; and
   determining the estimated pulse pressures further in response to determining that there is no change between the second pulse rate and the first pulse rate.

5. The method of claim 1, further comprising:
   determining a second pulse rate; and
   discarding measured changes of distension in response to determining that there is a change between the second pulse rate the first pulse rate.

6. The method of claim 1, wherein measuring the first change in distension of the artery without interfering with a pressure in the artery at the measurement location during the series of pulses includes applying a counter pressure that is below a diastolic pressure of the subject on or near the measurement location.

7. The method of claim 1, wherein measuring the first change in distension of the artery without interference to the arterial pressure in the artery at the measurement location during the series of pulses includes applying no man-made pressure to a portion of skin on the limb that is closest to the measurement location.

8. The method of claim 1, wherein the coefficient fitting the exponentially decaying function representing the exponential decay of the diastolic phase is an additive value applied.

9. The method of claim 1, further comprising:
   measuring, by the non-interfering arterial measurement sensor, a second change in distension of the artery from the measurement location on the limb without interference to the arterial pressure at the measurement location during an earlier series of pulses; and
   determining, by the processor, a second pulse rate and a preliminary blood pressure using the second change in distension, wherein determining the absolute blood pressure is in response to determining the first pulse rate is equal to the second pulse rate.

10. A device, comprising:
    a non-interfering arterial measurement sensor configured to measure a first change in distension of an artery at a measurement location on a limb of a subject without interference to an arterial pressure at the measurement location during a series of pulses; and
    a processor in communication with the non-interfering arterial measurement sensor, wherein the processor is configured with processor executable instructions to perform operations to:
    receive the first change in distension of the artery measured by the non-interfering arterial measurement sensor;
    determine a first pulse rate and estimated pulse pressures in response to receiving the first change in distension, the estimated pulse pressures comprising pressure values during at least a portion of a pulse including a diastolic phase;

determine a coefficient by curve fitting sensor measurements to an exponentially decaying function representing an exponential decay of a portion of the diastolic phase to select ones of the estimated pulse pressures corresponding to the diastolic phase, the coefficient indicative of a nonzero asymptotic value of the exponentially decaying function; and determine an absolute blood pressure by applying the coefficient to a select mathematical model expressing a first relationship between the first change in distension of the artery and a transmural pressure in the artery at the measurement location.

11. The device of claim 10, further comprising:

an elevation sensor in communication with the processor and configured to measure a change in elevation of the measurement location in response to moving the limb, wherein the processor is further configured with the processor executable instructions to perform operations to:

determine an incremental sensitivity between a second change in distension of the artery from the measurement location on the limb and a predicted change in the estimated pulse pressures after the change in elevation; and determine the estimated pulse pressures using another mathematical model describing a second relationship between changes in distension and the transmural pressure with the incremental sensitivity applied to the another mathematical model.

12. The device of claim 11, wherein the predicted change in distension is based on a last measured physiological parameter at a first elevation and a hydrostatic pressure change corresponding to the change in elevation.

13. The device of claim 10, wherein the processor is configured with the processor executable instructions to perform operations to:

determine a second pulse rate; and determine the estimated pulse pressures further in response to determining that there is no change between the second pulse rate and the first pulse rate.

14. The device of claim 10, wherein the processor is configured with the processor executable instructions to perform operations to:

determine a second pulse rate; and discard measured changes of distension in response to determining that there is a change between the second pulse rate the first pulse rate.

15. The device of claim 10, wherein measuring the first change in distension of the artery without interfering with a pressure in the artery at the measurement location during the series of pulses includes applying a counter pressure that is below a diastolic pressure of the subject on or near the measurement location.

16. The device of claim 10, wherein measuring the first change in distension of the artery without interference to the arterial pressure in the artery at the measurement location during the series of pulses includes applying no man-made pressure to a portion of skin on the limb that is closest to the measurement location.

17. The device of claim 10, wherein the coefficient fitting the exponentially decaying function representing the exponential decay of the diastolic phase is an additive value applied.

18. The device of claim 10, wherein the non-interfering arterial measurement sensor is further configured to measure a second change in distension of the artery from the measurement location on the limb without interference to the arterial pressure in the artery at the measurement location during an earlier series of pulses, and the processor is further configured with the processor executable instructions to perform operations to determine a second pulse rate and a preliminary blood pressure using the second change in distension, wherein determining the absolute blood pressure is in response to determining the first pulse rate is equal to the second pulse rate.

19. A device, comprising:

means for measuring a first change in distension of an artery at a measurement location on a limb of a subject without interference to an arterial pressure at the measurement location during a series of pulses;

means for determining a first pulse rate and estimated pulse pressures in response to measuring the first change in distension, the estimated pulse pressures comprising pressure values during at least a portion of a pulse including a diastolic phase;

determining a coefficient fitting an exponentially decaying function representing an exponential decay of a portion of the diastolic phase to select ones of the estimated pulse pressures corresponding to the diastolic phase, the coefficient indicative of a nonzero asymptotic value of the exponentially decaying function; and determining an absolute blood pressure by applying the coefficient to a select mathematical model expressing a first relationship between the first change in distension of the artery and a transmural pressure in the artery at the measurement location.

20. The device of claim 19, further comprising:

means for measuring a change in elevation of the measurement location in response to moving the limb;

means for determining an incremental sensitivity between a second change in distension of the artery from the measurement location on the limb and a predicted change in the estimated pulse pressures after the change in elevation; and means for determining the estimated pulse pressures using another mathematical model describing a second relationship between changes in distension and transmural pressure with the incremental sensitivity applied to the another mathematical model.

21. The device of claim 20, wherein the predicted change in distension is based on a last measured physiological parameter at a first elevation and a hydrostatic pressure change corresponding to the change in elevation.

22. The device of claim 19, further comprising:

means for determining a second pulse rate; and means for determining the estimated pulse pressures further in response to determining that there is no change between the second pulse rate and the first pulse rate.

23. The device of claim 19, further comprising:

means for determining a second pulse rate; and means for discarding measured changes of distension in response to determining that there is a change between the second pulse rate the first pulse rate.

24. The device of claim 19, wherein measuring the first change in distension of the artery without interfering with a pressure in the artery at the measurement location during the series of pulses includes applying a counter pressure that is below a diastolic pressure of the subject on or near the measurement location.

25. The device of claim 19, wherein measuring the first change in distension of the artery without interference to the arterial pressure in the artery at the measurement location during the series of pulses includes applying no man-made pressure to a portion of skin on the limb that is closest to the measurement location.

26. The device of claim 19, wherein the coefficient fitting the exponentially decaying function representing the exponential decay of the diastolic phase is an additive value applied.

27. The device of claim 19, further comprising:
means for measuring a second change in distension of the artery from the measurement location on the limb without interference to the arterial pressure at the measurement location during an earlier series of pulses; and
means for determining a second pulse rate and a preliminary blood pressure using the second change in distension, wherein determining the absolute blood pressure is in response to determining the first pulse rate is equal to the second pulse rate.

28. A non-transitory processor readable medium having stored thereon processor executable instructions configured to cause a processor to perform operations comprising:
determining a first pulse rate and estimated pulse pressures in response to a first change in distension of an artery at a measurement location on a limb of a subject, wherein the first change in distension is measured without interference to an arterial pressure at the measurement location during a series of pulses and the estimated pulse pressures comprise pressure values during at least a portion of a pulse including a diastolic phase;
determining, by the processor, a coefficient fitting an exponentially decaying function representing an exponential decay of a portion of the diastolic phase to select ones of the estimated pulse pressures corresponding to the diastolic phase, the coefficient indicative of a non-zero asymptotic value of the exponentially decaying function; and
determining, by the processor, an absolute blood pressure by applying the coefficient to a select mathematical model expressing a first relationship between the first change in distension of the artery and a transmural pressure in the artery at the measurement location.

29. The non-transitory processor readable medium of claim 28, wherein the processor executable instructions are configured to cause the processor to perform operations further comprising:
measuring, by an elevation sensor, a change in elevation of the measurement location in response to moving the limb;
determining an incremental sensitivity between a second change in distension of the artery from the measurement location on the limb, measured in response to the change in elevation of the measurement location in response to moving the limb, and a predicted change in the estimated pulse pressures after the change in elevation; and
determining the estimated pulse pressures using another mathematical model describing a second relationship between changes in distension and transmural pressure with the incremental sensitivity applied to the another mathematical model.

30. The non-transitory processor readable medium of claim 29, wherein the processor executable instructions are configured to cause the processor to perform operations such that the predicted change in distension is based on a last measured physiological parameter at a first elevation and a hydrostatic pressure change corresponding to the change in elevation.

31. The non-transitory processor readable medium of claim 28, wherein the processor executable instructions are configured to cause the processor to perform operations further comprising:
determining a second pulse rate; and
determining the estimated pulse pressures further in response to determining that there is no change between the second pulse rate and the first pulse rate.

32. The non-transitory processor readable medium of claim 28, wherein the processor executable instructions are configured to cause the processor to perform operations further comprising:
determining a second pulse rate; and
discarding measured changes of distension in response to determining that there is a change between the second pulse rate the first pulse rate.

33. The non-transitory processor readable medium of claim 28, wherein the processor executable instructions are configured to cause the processor to perform operations such that measuring the first change in distension of the artery without interfering with a pressure in the artery at the measurement location during the series of pulses includes applying a counter pressure that is below a diastolic pressure of the subject on or near the measurement location.

34. The non-transitory processor readable medium of claim 28, wherein the processor executable instructions are configured to cause the processor to perform operations such that measuring the first change in distension of the artery without interference to the arterial pressure in the artery at the measurement location during the series of pulses includes applying no man-made pressure to a portion of skin on the limb that is closest to the measurement location.

35. The non-transitory processor readable medium of claim 28, wherein the processor executable instructions are configured to cause the processor to perform operations such that the coefficient fitting the exponentially decaying function representing the exponential decay of the diastolic phase is an additive value applied.

36. The non-transitory processor readable medium of claim 28, wherein the processor executable instructions are configured to cause the processor to perform operations further comprising:
determining a second pulse rate and a preliminary blood pressure using a second change in distension of the artery from the measurement location on the limb measured by a non-interfering arterial measurement sensor without interference to the arterial pressure at the measurement location during an earlier series of pulses, wherein determining the absolute blood pressure is in response to determining the first pulse rate is equal to the second pulse rate.

* * * * *